United States Patent
Xu et al.

(10) Patent No.: US 7,304,199 B2
(45) Date of Patent: Dec. 4, 2007

(54) SOLID ACID CATALYST AND METHOD OF USING SAME

(75) Inventors: Jinsuo Xu, Hillsborough, NJ (US); Chuen Y. Yeh, Edison, NJ (US); Philip J. Angevine, Woodbury, NJ (US)

(73) Assignee: ABB Lummus Global Inc., Bloomfield, NJ (US)

( * ) Notice: Subject to any disclaimer, the term of this patent is extended or adjusted under 35 U.S.C. 154(b) by 447 days.

(21) Appl. No.: 10/824,390

(22) Filed: Apr. 14, 2004

(65) Prior Publication Data

US 2005/0234283 A1    Oct. 20, 2005

(51) Int. Cl.
*C07C 5/22* (2006.01)
*C07C 6/08* (2006.01)
*C07C 2/58* (2006.01)
*C01G 11/00* (2006.01)
*B01J 27/053* (2006.01)

(52) U.S. Cl. ............ 585/734; 585/708; 585/721; 208/113; 208/121; 502/217; 502/242; 502/255

(58) Field of Classification Search ............ 502/217, 502/219, 220, 221, 242, 254–257, 263, 308–310, 502/313, 319–323, 327, 333, 334, 339, 349–352, 502/407, 415, 439; 585/708, 721, 734; 208/113, 208/121
See application file for complete search history.

(56) References Cited

U.S. PATENT DOCUMENTS

| | | | |
|---|---|---|---|
| 3,799,979 | A | 3/1974 | Hensel et al. |
| 4,725,572 | A | 2/1988 | Sera et al. |
| 5,053,374 | A | 10/1991 | Absil et al. |
| 5,422,327 | A | 6/1995 | Soled et al. |
| 5,500,109 | A | 3/1996 | Keville et al. |
| 5,993,643 | A | 11/1999 | Chang et al. |
| 6,080,904 | A | 6/2000 | Chang et al. |
| 6,107,235 | A | 8/2000 | Matsuzawa |
| 6,479,691 | B1 * | 11/2002 | Sasaki et al. ............... 558/321 |
| 6,767,859 | B2 * | 7/2004 | Ying et al. ................. 502/305 |
| 7,053,260 | B2 * | 5/2006 | Xu et al. .................... 585/638 |
| 7,125,536 | B2 * | 10/2006 | Fu et al. ................... 423/592.1 |
| 2003/0069131 | A1 | 4/2003 | Ying et al. |

* cited by examiner

*Primary Examiner*—Cam N. Nguyen
(74) *Attorney, Agent, or Firm*—Dilworth & Barrese, LLP

(57) ABSTRACT

A catalyst composition includes an oxygen compound of an element selected from Group IVB or Group IVA of the Periodic Table of the Elements; an oxygen compound of an element selected from Group VIB or Group VIA of the Periodic Table of the Elements; and at least about 1% by weight based upon total catalyst weight of fumed silica particles. The catalyst composition is advantageously employed in hydrocarbon conversion processes such as isomerization.

23 Claims, No Drawings

SOLID ACID CATALYST AND METHOD OF USING SAME

BACKGROUND

1. Field of the Invention

The present invention relates to a catalyst for use in hydrocarbon conversion processes, and more particularly to the preparation of anion modified solid acid catalysts.

2. Background of the Art

Solid acid catalysts are used in a wide variety of chemical conversion processes in the oil refining and petrochemical industries. Particularly, anion modified oxides such as $WO_3/ZrO_2$, $SO_4^{-2}/ZrO_2$, $MoO_3/ZrO_2$, $SO_4^{-2}/TiO_2$, and $SO_4^{-2}/SnO_2$, are strong solid acids and have shown promising performance in hydrocarbon conversion processes such as, for example, isomerization, catalytic cracking, alkylation and transalkylation. See for example, U.S. Pat. Nos. 6,107,235 and 6,080,904.

U.S. patent application Publication No. 2003/0069131 discloses a solid acid catalyst comprising a compound of anion-modified metal oxide doped with metal ions and a method of isomerizing an alkane using the catalyst.

Catalysts prepared in accordance with prior art methods are in powder form and are not suitable for loading into most of the commercial reactors, which require catalysts formed into granules, spheres or extrudates with good mechanical strength while retaining high activity.

The solid acid catalysts mentioned above can be admixed with binders such as alumina, clay, or silica to provide shaped catalyst particles with good mechanical strength. However, the activity of the shaped bound catalysts for alkane isomerization—particularly n-heptane isomerization—is reduced significantly as compared with the unbound powder form. Accordingly, what is needed is a catalyst/binder composition which has high mechanical strength and good catalytic performance.

SUMMARY

A catalyst composition is provided herein which comprises an oxygen compound of an element selected from Group IVB or Group IVA of the Periodic Table of the Elements; an oxygen compound of an element selected from Group VIB or Group VIA of the Periodic Table of the Elements; and at least about 1% by weight based upon total catalyst weight of fumed silica particles.

The catalyst composition is advantageously employed in hydrocarbon conversion processes such as isomerization, catalytic cracking, alkylation and transalkylation.

DETAILED DESCRIPTION OF PREFERRED EMBODIMENT(S)

The present invention employs fumed silica as a binder component for the shaping of powder mixed oxide catalysts to achieve a shaped catalyst with excellent physical strength and enhanced catalyst performance for alkane isomerization. The final shape of the catalyst can be, for example, an extrudate, sphere, or tablet.

More particularly, the catalyst of the present invention comprises an oxygen compound of one or more elements of Group IVA or IVB (CAS notation) of the Periodic Table of the Elements. Group IVB elements include titanium (Ti), zirconium (Zr) and hafnium (Hf). Group IVA elements include carbon (C), silicon (Si), germanium (Ge), tin (Sn) and lead (Pb).

The catalyst further includes an oxygen compound of a Group VIB or Group VIA element of the Period Table. Group VIB elements include chromium (Cr), molybdenum (Mo) and tungsten (W). Group VIA, elements include sulfur (S), selenium (Se) and tellurium (Te).

The mass ratio of the Group IVB or IVA compound to the Group VIB or VIA compound can typically range from about 0.001 to 1000, preferably 0.1 to about 100, and more preferably from about 1 to about 10. Preferred catalyst combinations include, for example, $WO_3/ZrO_2$, $SO_4^{-2}/ZrO_2$, $MoO_3/ZrO_2$, $SO_4^{-2}/TiO_2$, and $SO_4^{-2}/SnO_2$.

The catalyst can be modified by the inclusion of a dopant selected from compounds of aluminum, gallium, cerium, antimony, scandium, magnesium, cobalt, iron, chromium, yttrium and/or indium. In a preferred embodiment the catalyst includes an aluminum doped zirconia combined with tungsten oxide, designated as $WO_3/Al—ZrO_2$.

The catalyst can also include a Group VIII noble metal component such as platinum, palladium or iridium.

The binder of the present invention contains fumed silica. Fumed silica is prepared by the vapor phase decomposition of halosilane (e.g., silicon tetrachloride) in a hydrogen-oxygen flame. The combustion process produces silicon dioxide molecules which condense to form particles. The particles collide and sinter together. The primary particles have a diameter ranging from about 9 nm to about 30 nm. However, the primary particles fuse together to form aggregates (the smallest dispersable units) of from about 0.2 to about 0.3 microns in particle size. The aggregates, in turn, tend to entangle together to form agglomerates of from about 30 to about 44 microns in particle size. Fumed silica is amorphous. The individual particles are non-porous. However, the agglomerates have a very high void volume (>98%). The BET surface area of fumed silica typically ranges from about 160 $m^2/g$ to about 200 $m^2/g$. Fumed silica suitable for use in the invention can be obtained under the designation AEROSIL® from Degussa Co., or under the designation CAB-O-SIL® from the Cabot Corporation. As shown below, fumed silica provides surprisingly better results for alkane isomerization as compared with other silica or alumina binders. At least about 1% by weight of fumed silica is incorporated into the final mixed oxide/binder catalyst composition, preferably at least about 5%, and more preferably at least about 10%. As demonstrated below, the fumed silica is surprisingly superior to colloidal silica as a binder.

Colloidal silica includes amorphous silica particles having a size usually of less than about 100 microns. The aggregate particle size can be as small as the size of the primary particles. The surface of the colloidal silica particles typically consists of silanols having hydroxyl groups attached to the silicon atoms, e.g., $Si—(OH)_x$, or siloxanes, e.g., $Si—O—Si—O—$. Colloidal silica is typically produced by adjusting the pH of a sodium silicate solution, for example by cation exchange, to form a silica sol. The sol is then stabilized with cations such as sodium or ammonium. Colloidal silica is provided in aqueous liquid form rather than in powder form.

The feedstock for the present process may be one which contains significant amounts of $C_5+$ normal and/or slightly branched paraffins. In addition, the feedstock may contain monocyclic aromatic compounds and/or cyclic paraffins, such as cyclohexane.

The present catalyst may be used to isomerize $C_4$-$C_8$ paraffin hydrocarbons, either as pure compounds or mixtures. In refinery operations, the paraffins will normally be present in mixtures and, in addition to the $C_4$-$C_8$ materials, may contain hydrocarbons boiling outside this range. Cycloparaffins and aromatics may also be present. Thus, the feed can comprise $C_4$-$C_8$ paraffins such as butane, pentane, hexane and these may be present in refinery streams such as raffinate cuts from solvent extraction units and reformer feedstock. The feeds may also contain cyclic hydrocarbons, e.g., in the form of $C_6$+ naphthas. The cyclic materials in such feeds may undergo ring opening and isomerization reactions in the presence of the catalyst with its associated metal component, to form paraffins which then undergo isomerization to iso-paraffins which can be separated from the cyclics by fractionation, with the cyclics being recycled to extinction. For example, cyclohexane can be converted to methyl cyclopentane. In addition to pure paraffin feeds ($C_4$-$C_8$), mixed paraffin-olefin feeds containing significant levels of olefin may be utilized.

The isomerization is carried out in the presence of the catalyst, preferably in the presence of hydrogen. Reaction temperatures are suitably in the range of about 77° F. to 800° F. (about 25° C. to 425° C.). Temperatures outside this range may be utilized although they are normally less preferred. Typical temperatures range from about 200° F. to 600° F. (about 43° C. to 316° C.). Pressures can typically range from about 1 psig up to about 1,500 psig (about 7,000 kPa), although higher pressures can also be used. Lower pressures, in the range of about 50 to 500 psig (about 350 kPa to 3,500 kPa) may readily be employed; and the use of relatively low pressures within this range will generally be preferred in order to permit the use of low pressure equipment. The isomerization is usually carried out in the presence of hydrogen, typically at a molar ratio relative to the feed from 0.01 to 10:1 and usually from 0.5:1 to 2:1. Space velocities are typically from 0.1 to 10 LHSV and usually from 0.5 to 5.0 LHSV. When an additional acidic material (Lewis acid or Bronsted acid) is included in the catalyst, lower operational temperatures may be used, favoring the isomerization over the less desired cracking reactions.

Examples and comparative examples are provided below to illustrate the invention and its advantages. The Examples illustrate the invention. The Comparative Examples do not illustrate the invention, but are provided to illustrate by way of comparison the unexpected advantages achieved by the invention as opposed to non-inventive catalysts. An aluminum-doped mixed oxide catalyst containing a platinum component was prepared in accordance with the following procedure.

Mixed zirconium-aluminum hydroxides were prepared by the co-precipitation of 13 parts by weight of $ZrOCl_2.8H_2O$ and 0.75 parts of $Al(NO_3)_3.9H_2O$ with 80 parts of 14% aqueous ammonium hydroxide solution. The mixed hydroxides precipitate was washed four times with distilled water followed by filtration. After drying the precipitate at 100-120° C., the filter cake was pulverized into a fine powder. The mixed hydroxide powder was then impregnated with 8.4 parts of ammonium metatungstate solution, $(NH_4)_6H_2W_{12}O_{40}$, after which the mixture was then dried at 100-120° C. and then calcined at 800° C. for 3 hours. The product was a yellowish powder of tungstated aluminum doped zirconia designated as $WO_3/Al$—$ZrO_2$, which was used in all examples.

The shaped catalyst was formed by combining the tungstated aluminum doped zirconia with the binder, shaping and then calcining, as indicated.

To incorporate the noble metal into this material the tungstated aluminum doped zirconia was impregnated with aqueous solution of $(NH_3)_4Pt(NO_3)_2$. This mixture was dried and then calcined at 350° C. for 3 hours, whereupon the platinum salt decomposed to platinum oxide $PtO_2$. This catalyst was designated as $Pt/WO_3/Al$—$ZrO_2$. In some tests the platinum was added prior to shaping with binder. In other tests the platinum was added after shaping with binder.

The catalyst performance was evaluated in an n-heptane isomerization reaction conducted in a fixed bed reactor. The shaped catalyst was pulverized to adapt to the laboratory reactor. The amount of catalyst/binder sample varied according to the amount of binder, but in all cases the total amount of active $WO_3/Al$—$ZrO_2$ was maintained at about 500 mg. The catalyst was loaded into a ½ inch o.d. quartz tube reactor with a thermocouple located below the catalyst bed. The catalyst was heated in flowing helium with a 10° C./min ramp rate to 350° C. and held for 60 minutes. Then the helium flow was replaced with hydrogen, and the catalyst was reduced in hydrogen at 350° C. for 2 hours. At the end of the reduction the reactor temperature was lowered to 200° C. Then a feed gas containing 3 mole percent of n-heptane in hydrogen was introduced into the reactor. The reaction products were analyzed by an on-line gas chromatograph with an FID detector and a 50 mm, 0.53 micron alumina capillary column. The first product sample was taken 15 minutes after the feed was introduced. Subsequent samples were analyzed at 45 minute intervals. The catalyst activity and selectivity were calculated from summing the peak areas of products and the reactants according to the following equations 1 and 2, respectively:

$$\text{Conversion \%} = 100 \Sigma P_A / \Sigma (P_A + P_B) \quad [1]$$

and $$\text{Selectivity \%} = 100 \Sigma P_C / \Sigma P_A \quad [2]$$

wherein:

$P_A$ is the peak areas of all products;

$P_B$ is the unconverted n-$C_7$ peak area; and, $P_C$ is the peak areas of branched heptanes.

COMPARATIVE EXAMPLE 1

This comparative example illustrates the preparation and performance testing of tungstated aluminum-doped zirconia with platinum added. No binder was employed. 18 Parts of the material obtained from example 1 was impregnated with 6.21 parts of 1.74 wt % of $(NH_3)_4Pt(NO_3)_2$ aqueous solution. After calcination at 350 C for 3 hours, the platinum salt decomposed into platinum oxide. The sample was designated as 0.6% $Pt/WO_3/Al$—$ZrO_2$ and used for the performance test described above. The results are shown in Table 1.

COMPARATIVE EXAMPLE 2

This comparative example illustrates the preparation and performance characteristics of colloidal alumina-bound mixed oxide catalyst. The $Pt/WO_3/Al$—$ZrO_2$ catalyst was prepared in accordance with Comparative Example 1 except that the platinum content was adjusted to 1.0 wt %. A shaped catalyst with 80% mixed-oxide/20% alumina was prepared by mixing 8.0 parts of $Pt/WO_3/Al$—$ZrO_2$ prepared according to Comparative Example 1 and 10.0 parts of Nyacol colloidal alumina (20% alumina in aqueous medium). The mixture was pressed in a "dough-like" form and subsequently calcined. The calcination condition was: static air, 120° C. for 1 hour, raised to 400° C. with a ramp rate of 5° C./min and held for 3 hours. The resulting material was pulverized to fine powder and used for evaluation of n-heptane isomerization in the manner indicated above. The results are shown in Table 1.

COMPARATIVE EXAMPLE 3

This comparative example illustrates the preparation and isomerization performance characteristics of colloidal silica-bound mixed oxide catalyst. The Pt/WO$_3$/Al—ZrO$_2$ catalyst was prepared in accordance with Comparative Example 1 to provide 0.6% Pt. A colloidal silica source containing 40 wt % SiO$_2$ in an aqueous medium (Nalco-2327) was obtained from ONDEO Nalco Company, Chicago, Ill. Two parts of 0.6% Pt/WO$_3$/Al—ZrO$_2$ prepared in Comparative Example 1 was mixed with 1.2 parts of Nalco-2327. The mixture was pressed in a "dough-like" form and subsequently calcined. The calcination conditions were: static air, 120° C. for 12 hours, raised to 400° C. with ramp rate of 5° C./min and held for 3 hours, and cooled to room temperature. The catalyst was pulverized to fine powder and used for isomerization performance evaluation in accordance with the procedures described above. The results are shown in table 1.

COMPARATIVE EXAMPLE 4

This comparative example illustrates the preparation and isomerization performance characteristics of Boehmite alumina-bound mixed oxide catalyst. The platinum was added after shaping. Catapal® "D" alumina (Boehmite) was obtained from SASOL North American Inc. Two hundred seventy two (272) parts of WO$_3$/Al—ZrO$_2$ prepared according to the procedure set forth above, was mixed with 117 parts of Catapal® "D" alumina, 135 parts of deionized water, and 3.13 parts of 70% nitric acid. The mixture was mixed in a mixing devise thoroughly, and then transferred into the cylinder of a hydraulics extruder (Loomis Ram Extruder, Model 232-16) followed with extrusion into 1/16" diameter extrudates. The extrudates were calcined under the following conditions: static air, 90° C. for 1 hour; 120° C. for 1 hour, raised to 500° C. with a ramp rate of 5° C./min and held for 5 hours, and cooled to room temperature. The extrudates were found to have a crush strength of 2.9 lb/mm as tested in accordance with ASTM D4179 (Test Method for Single Pellet Crush Strength of Formed Catalyst Shapes). Then, 0.6 wt % of platinum was loaded on this extrudate following the procedure in Comparative Example 1. The extrudates were pulverized into a powder prior to being loaded in the reactor. The isomerization test results are shown in Table 1.

COMPARATIVE EXAMPLE 5

This comparative example illustrates the preparation and isomerization performance characteristics of precipitated silica-bound mixed oxide catalyst. The Pt/WO$_3$/Al—ZrO$_2$ catalyst was prepared in accordance with Comparative Example 1 to provide 0.6% Pt. Precipitated silica (Hi-Sil 233) was obtained from PPG Industries Inc., Pittsburg, Pa. This Hi-Sil 233 silica contains 0.55 wt % Na. Since Na could significantly deteriorate the catalyst acidity, the "as is" Hi-Sil 233 was washed thoroughly to lower the Na level below 300 ppm prior to mixing with the WO$_3$/Al—ZrO$_2$ powder. 2.4 Parts of WO$_3$/Al—ZrO$_2$ were mixed with 0.6 parts of washed Hi-Sil 233. The mixture was pressed in a "dough-like" form and subsequently calcined. The calcination conditions were: static air, 120° C. for 6 hours, raised to 450° C. with ramp rate of 5° C./min and held for 5 hours, and cooled to room temperature. The mechanical strength of the calcined particles was estimated to be less than 1.9 lb/mm based on the ease of manual breakage. Then the calcined material was pulverized into powder and loaded with 0.6 wt % Pt following procedure in Comparative Example 1. The results are shown in table 1.

TABLE 1

| | Comparative Example | | | | |
|---|---|---|---|---|---|
| | 1 | 2 | 3 | 4 | 5 |
| Binder Material | None | Colloidal Alumina | Colloidal silica | Catapal ® D alumina (Boehmite) | Precipitated silica |
| Binder amount (wt %) | 0 | 20 | 20 | 30 | 20 |
| Calcination | — | 400° C., 3 hr | 400° C., 3 hr | 500° C., 5 hr | 450°C., 5 hr |
| Physical Properties* | | | | | |
| Pt (wt %) added prior/after shaping | 0.6 | 1.0 prior to shaping | 0.6 prior to shaping | 0.6 after shaping | 0.6 after shaping |
| Pt Dispersion (%) | 21 | 17 | 17 | 33 | 15 |
| Surface Area (m$^2$/g) | 51 | 105 | 69 | 121 | 60 |
| Pore Volume (cc/g) | 0.16 | 0.27 | 0.21 | 0.29 | 0.24 |
| Avg. Pore Diameter (nm) | 9.4 | 8.8 | 10.0 | 7.4 | 16.2 |
| Catalytic Performance | | | | | |
| n-C7 Conversion (%) | 38.4 | 9.1 | 5.8 | 13.4 | 34.7 |
| Isomer selectivity (%) | 98.0 | 44.3 | 91.6 | 60.3 | 98.2 |

*Pt dispersion was determined by CO chemisorption; Surface area is BET surface area calculated from N2 adsorption-desorption data; Pore volume comes from single point total pore volume at P/P$_0$ = 0.9829; Average pore diameter comes from BJH desorption average pore diameter.

EXAMPLE 1

This example illustrates the preparation and isomerization performance characteristics of the fumed silica-bound mixed oxide catalyst of the present invention. The platinum was incorporated into the catalyst prior to shaping. AEROSIL® brand fumed SiO$_2$ (AEROSIL 200) was obtained from Degussa Corporation. 2.4 Parts of 0.6% Pt/WO$_3$/Al—ZrO$_2$ prepared in Comparative Example 1 was mixed with 0.11 parts of AEROSIL 200 and 0.28 parts of deionized water. The mixture was pressed in a "dough-like" form and subsequently calcined. The calcination conditions were: static air, 90° C. for 1 hour, 120° C. for 1 hour, raised to 450° C. with a ramp rate of 5° C./min and held for 5 hours, cooled to room temperature. The material was pulverized to a fine powder and used for isomerization performance evaluation according to the procedure indicated above. The results are shown in Table 2.

EXAMPLE 2

This example illustrates the preparation and isomerization performance characteristics of the fumed silica-bound mixed oxide catalyst of the present invention. The platinum was added to the catalyst after shaping. AEROSIL® $SiO_2$ (AEROSIL 200) was obtained from Degussa Corporation. 7.2 Parts of $WO_3/Al$—$ZrO_2$ was mixed with 0.33 parts of AEROSIL 200 and 2.75 parts of deionized water. The mixture was pressed in a "dough-like" form and subsequently calcined. The calcination conditions were: static air, 120° C. for 1 hour, raised to 450° C. with ramp rate of 5° C./min and held for 5 hours. Then, the calcined material was pulverized into powder and then loaded with 0.6 wt % Pt following procedure in Comparative Example 1. The results of isomerization performance evaluation are shown in Table 2.

EXAMPLE 3

This example illustrates the preparations and isomerization performance characteristics of the fumed silica-bound mixed oxide catalyst of the present invention. The platinum was added after shaping. AEROSIL® $SiO_2$ (AEROSIL 200) was obtained from Degussa Corporation. 8.0 Parts of $WO_3/Al$—$ZrO_2$ was mixed with 2.0 parts of AEROSIL 200 and 5.25 parts of deionized water. The mixture was pressed into a "dough-like" form and subsequently calcined. The calcination conditions were: static air, 120° C. for 1 hour, raised to 450° C. with a ramp rate of 5° C./min and held for 5 hours. Then the calcined material was pulverized into powder and loaded with 0.6 wt % Pt following procedure in Comparative Example 1. The performance test results are shown in Table 2.

EXAMPLE 4

This example illustrates the preparation and isomerization performance characteristics of the fumed silica bound mixed oxide catalyst of the present invention. The platinum was added after shaping. AEROSIL® $SiO_2$ (AEROSIL 200) was obtained from Degussa Corporation. 8.0 Parts of $WO_3/Al$—$ZrO_2$ was mixed with 2.0 parts of AEROSIL200 and 5.25 parts of deionized water. The mixture was pressed in a "dough-like" form and subsequently calcined. The calcination conditions were: static air, 120° C. for 1 hour, raised to 550° C. with a ramp rate 5° C./min and held for 5 hours. Then the calcined material was pulverized into powder and loaded with 0.6 wt % Pt following procedure in Comparative Example 1. The isomerization performance test results are shown in Table 2.

EXAMPLE 5

This example illustrates the preparations and isomerization performance characteristics of the fumed silica-bound mixed oxide extrudate catalyst of the present invention. The platinum was added after shaping. AEROSIL® $SiO_2$ (AEROSIL 200) was obtained from Degussa Corporation. 320.0 Parts of $WO_3/Al$—$ZrO_2$ was mixed with 80.0 parts of AEROSIL 200 and ~180 parts of deionized water. The mixture was mixed in a mixing devise thoroughly, and then transferred into the cylinder of a hydraulics extruder (Loomis Ram Extruder, Model 232-16) followed with extrusion into 1/16" diameter extrudates. The calcination conditions for the extrudates were: static air, 120° C., raised to 450° C. with a ramp rate of 10° C./min and held for 5 hours. This calcined extrudates has crush strength of 1.9 lb/mm (following ASTM D4179 Test Method for Single Pellet Crush Strength of Formed Catalyst Shapes). Then, 0.6 wt % of platinum was loaded on this extrudate following the procedure in Comparative Example 1. The extrudates was pulverized into powder prior to being loaded in the reactor. The performance test results are shown in Table 2.

TABLE 2

| | Example | | | | |
|---|---|---|---|---|---|
| | 1 | 2 | 3 | 4 | 5 |
| Binder Material | Fumed silica | Fumed silica | Fumed silica | Fumed silica | Fumed silica |
| Binder Amount (wt. %) | 4.4 | 4.4 | 20 | 20 | 20 |
| Calcination | 450° C., 5 hr | 450° C., 5 hr | 450° C., 3 hr | 550° C., 5 hr | 450° C., 5 hr |
| Physical Properties* | | | | | |
| Pt (wt %) added prior/after shaping | 0.6 prior to shaping | 0.6 after shaping | 0.6 after shaping | 0.6 after shaping | 0.6 after shaping |
| Pt Dispersion (%) | 15 | 21 | 17 | 23 | 21 |
| Surface Area ($m^2/g$) | 59 | 59 | 85 | 82 | 78 |
| Pore Volume (cc/g) | 0.21 | 0.20 | 0.28 | 0.30 | 0.25 |
| Avg. Pore Diameter (nm) | 11.5 | 10.8 | 11.7 | 12.4 | 12.8 |
| Catalytic Performance | | | | | |
| n-C7 Conversion (%) | 70.3 | 57.1 | 57.7 | 59.7 | 47.6 |
| Isomer Selectivity (%) | 94.7 | 97.4 | 97.1 | 97.6 | 98.1 |

*Pt dispersion was determined by CO chemisorption; Surface area is BET surface area calculated from N2 adsorption-desorption data; Pore volume comes from single point total pore volume at $P/P_0 = 0.9829$; Average pore diameter comes from BJH desorption average pore diameter.

EXAMPLE 6

This example illustrates the preparation and isomerization performance characteristics of the mixed binder—fumed silica/colloidal silica-bound mixed oxide catalyst of the present invention. The platinum was added after shaping. AEROSIL® $SiO_2$ (AEROSIL 200) was obtained from Degussa Corporation. A colloidal silica source containing 40 wt % $SiO_2$ in an aqueous medium (Nalco-2327) was obtained from ONDEO Nalco Company, Chicago, Ill. 2.40 Parts of $WO_3/Al$—$ZrO_2$ was mixed with 0.48 parts of AEROSIL 200, 0.30 parts of Nalco-2327, and proper amount of deionized water. The mixture was pressed into a "dough-like" form and subsequently calcined. The calcination conditions were: static air, 120° C. for 6 hour, raised to 450° C. with a ramp rate of 5° C./min and held for 5 hours. Then the calcined material was pulverized into powder and loaded with 0.6 wt % Pt following procedure in Comparative Example 1. The performance test results are shown in Table 3.

EXAMPLE 7

This example illustrates the preparations and isomerization performance characteristics of another mixed binder—fumed silica/Catapal® "D" alumina bound mixed oxide catalyst of the present invention. The platinum was added after shaping. AEROSIL® $SiO_2$ (AEROSIL 200) was obtained from Degussa Corporation. Catapal® "D" alumina (Boehmite) was obtained from SASOL North American Inc. 2.40 Parts of $WO_3/Al$—$ZrO_2$ was mixed with 0.48 parts of AEROSIL 200, 0.12 parts of Catapal® "D" alumina, and proper amount of deionized water. The mixture was pressed into a "dough-like" form and subsequently calcined. The calcination conditions were: static air, 120° C. for 6 hour, raised to 450° C. with a ramp rate of 5° C./min and held for 5 hours. Then the calcined material was pulverized into powder and loaded with 0.6 wt % Pt following procedure in Comparative Example 1. The performance test results are shown in Table 3.

TABLE 3

| | Example | |
|---|---|---|
| | 1 | 2 |
| Binder Material | Fumed silica + colloidal silica | Fumed silica + Catapal ® "D" alumina |
| Binder amount (wt. %) | 20 | 20 |
| Calcination | 450° C., 5 hr | 450° C., 5 hr |
| Physical Properties* | | |
| Pt (wt %) added | 0.6 | 0.6 |
| prior/after shaping | after shaping | after shaping |
| Pt Dispersion (%) | 16 | 24 |
| Surface Area (m²/g) | 74 | 80 |
| Pore Volume (cc/g) | 0.27 | 0.29 |
| Avg. Pore Diameter (nm) | 14.6 | 14.5 |
| Catalytic Performance | | |
| n-C7 Conversion (%) | 49.1 | 47.5 |
| Isomer Selectivity (%) | 98.8 | 98.7 |

*Pt dispersion was determined by CO chemisorption; Surface area is BET surface area calculated from N2 adsorption-desorption data; Pore volume comes from single point total pore volume at $P/P_0 = 0.9829$; Average pore diameter comes from BJH desorption average pore diameter.

The above results show that the fumed silica bound mixed oxide catalyst of the present invention (Examples 1-5) had better n-$C_7$ conversion than the unbound catalyst of Comparative Example 1, whereas the colloidal silica and alumina-bound catalysts of Comparative Examples 2-4 performed worse (i.e., lower n-$C_7$ conversion and selectivity than the unbound catalyst of Comparative Example 1. The shaped catalyst using precipitated silica as binder has low mechanical strength but exhibits fair isomerization activity (Comparative Example 5).

Moreover, it would be preferable to incorporate the platinum after shaping to prevent sintering of the precious metal during calcining. For example, the catalyst of Comparative Example 4, with platinum loaded after shaping, performed better in terms of n-$C_7$ conversion than the catalysts of Comparative Examples 2 and 3, with platinum loaded prior to shaping. However, it was surprisingly found that when fumed silica was employed as the binder, incorporation of the platinum prior to shaping (Example 1) provided a catalyst having n-$C_7$ conversion superior to that of even Examples 2, 3 and 4. These results indicate that fumed silica is indeed an excellent binder for the mixed oxide isomerization catalysts of the invention.

We have also explored binding $WO_3/Al$—$ZrO_2$ powder using the mixture of fumed silica and other low cost binders, such as colloidal silica or Catapal® "D" alumina. The test results are listed in Table 3. The overall catalyst activity are comparable or even higher than the unbound catalyst in term of activity per total catalyst weight. The extrudate using pure fumed silica (Example 5 of Table 2) has a crush strength of 1.9 lb/mm. When higher crush strength of catalyst is needed, a mixed binder would be a good alternative in place of pure fumed silica.

The Pt dispersion, surface area, pore volume, and pore size of the catalyst varies with different binder and calcination conditions. However, there is no consistent correlation between catalyst activity/selectivity and the factors mentioned above. From side by side comparison, it is clear that the superior catalyst performance in fumed silica bound samples is owing to the binder material itself. While we do not wish to be bound to any particular theory, one possible explanation for these phenomena might be related to the interaction of the binder with the active center of $Pt/WO_3/Al$—$ZrO_2$. Fumed silica has lower surface density of hydroxyl groups than precipitated silica and colloidal silica, therefore the interaction between fumed silica and $Pt/WO_3/Al$—$ZrO_2$ will be relatively weaker. Strong interaction may reduce the acidity of the catalyst.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A catalyst composition comprising:
   a) an oxygen compound of an element selected from Group IVB or Group IVA of the Periodic Table of the Elements;
   b) an oxygen compound of an element selected from Group VIB or Group VIA of the Periodic Table of the Elements; and
   c) a catalytic performance enhancing binder comprising at least about 1% by weight, based upon total catalyst weight, of fumed silica particles
   wherein said catalyst in the form of catalyst particles having a predetermined shape.

2. The catalyst composition of claim 1 wherein the fumed silica comprises at least about 5% by weight of the total catalyst weight.

3. The catalyst composition of claim 1 further including an aluminum compound.

4. The catalyst composition of claim 3 wherein the aluminum compound is aluminum oxide.

5. The catalyst composition of claim 1 further including a Group VIII metal.

6. The catalyst composition of claim 5 wherein the Group VIII metal is selected from the group consisting of platinum and palladium.

7. The catalyst composition of claim 1 wherein the Group IVB element is tin.

8. The catalyst composition of claim 1 wherein the Group IVA element is selected from the group consisting of titanium and zirconium.

9. The catalyst composition of claim 1 wherein the Group VIB element is molybdenum or tungsten.

10. The catalyst composition of claim 1 comprising tungsten oxide and zirconium oxide.

11. The catalyst composition of claim 1 comprising molybdenum oxide and zirconium oxide.

12. The catalyst composition of claim 1 comprising a sulfate and zirconium oxide.

13. The catalyst composition of claim 1 comprising a sulfate and titanium oxide.

14. The catalyst composition of claim 1 comprising a sulfate and tin oxide.

15. The catalyst composition of claim 1 wherein the fumed silica is admixed with colloidal silica.

16. The catalyst composition of claim 1 wherein the fumed silica is admixed with alumina.

17. The catalyst of claim 1 wherein the fumed silica is admixed with precipitated silica.

18. The catalyst composition of claim 1 wherein the catalyst particles are in the form of extrudates, spheres or tablets.

19. A process for the chemical conversion of a hydrocarbon comprising contacting the hydrocarbon under chemical conversion reaction conditions with a catalyst composition which comprises:
   i) an oxygen compound of an element selected from Group IVB or Group IVA of the Periodic Table of the Elements;
   ii) an oxygen compound of an element selected from Group VIB or Group VIA of the Periodic Table of Elements; and
   iii) a catalytic performance enhancing binder comprising at least about 1% by weights based upon total catalyst weights of fumed silica particles,
   wherein said catalyst is in the form of catalyst particles having a predetermined shape.

20. The process of claim 19 wherein the chemical conversion process is selected from the group consisting of isomerization, catalytic cracking, alkylation and transalkylation.

21. The process of claim 20 wherein the chemical conversion process is isomerization and the chemical conversion conditions comprise a temperature of from about 93° C. to about 425° C., a pressure of from about 1 psig to about 1,000 psig, and a LHSV of from about 0.1 to about 10.

22. The process of claim 21 wherein the hydrocarbon is selected from the group consisting of n-butane, n-pentane, n-hexane, cyclohexane, n-heptane, n-octane, n-nonane and n-decane.

23. The process of claim 22 wherein the catalyst composition comprises tungsten oxide, zirconium oxide, aluminum oxide and platinum.

* * * * *